United States Patent [19]

De Barbieri

[11] 4,314,999
[45] Feb. 9, 1982

[54] N-ACYL DERIVATIVES OF GLUCOSAMINE HAVING ANTITUMOR CHEMOTHERAPEUTIC ACITIVITY

[75] Inventor: Augusto De Barbieri, Milan, Italy

[73] Assignee: Proter S.p.A., Milan, Italy

[21] Appl. No.: 173,621

[22] Filed: Jul. 30, 1980

Related U.S. Application Data

[63] Continuation-in-part of Ser. No. 929,237, Jul. 31, 1978, Pat. No. 4,216,208.

[51] Int. Cl.³ ............... A61K 37/02; C07C 103/52
[52] U.S. Cl. .......................... 424/177; 260/112.5 R; 424/180; 536/4; 536/18; 536/53
[58] Field of Search ............. 424/177, 180; 260/112.5 R; 536/18, 53, 4

[56] References Cited

U.S. PATENT DOCUMENTS

| | | | |
|---|---|---|---|
| 4,211,866 | 7/1980 | Matsumura et al. | 536/53 |
| 4,216,208 | 8/1980 | De Barbieri | 260/112.5 R |
| 4,220,643 | 9/1980 | Suami | 424/180 |
| 4,229,440 | 10/1980 | Murofushi et al. | 424/180 |
| 4,232,149 | 11/1980 | Paegle et al. | 536/23 |
| 4,237,266 | 12/1980 | Sugiura et al. | 536/1 |
| 4,239,905 | 12/1980 | Kodama et al. | 536/29 |
| 4,241,052 | 12/1980 | Tsujihara et al. | 424/180 |
| 4,243,663 | 1/1981 | Azuma et al. | 424/181 |
| 4,248,999 | 2/1981 | Baba et al. | 536/4 |
| 4,254,110 | 3/1981 | Cassinelli et al. | 424/180 |

OTHER PUBLICATIONS

Chaturvedi et al., J.A.C.S. 1966, pp. 971–973.
Adam et al., Biochem. and Biophys. Res. Commun. 72, 1976, pp. 339–346.
Gregoriadis, Nature, Feb. 3, 1977, vol. 265, pp. 407–410.
De Barbieri, Current Chemotherapy, American Society of Microbiology, Apr. 1978, pp. 1183–1185.

Primary Examiner—Blondel Hazel
Attorney, Agent, or Firm—Fisher, Christen & Sabol

[57] ABSTRACT

N-acyl derivatives of D-hexosamine made by linking an oligopeptide having a m-di(2-chloroethyl)amino-L-phenylalanyl residue to the amino groups of two hexosamine molecules by a peptide bond, are endowed with strong antitumor action against transplanted neoplasms in animals. Compounds according to the present invention are:

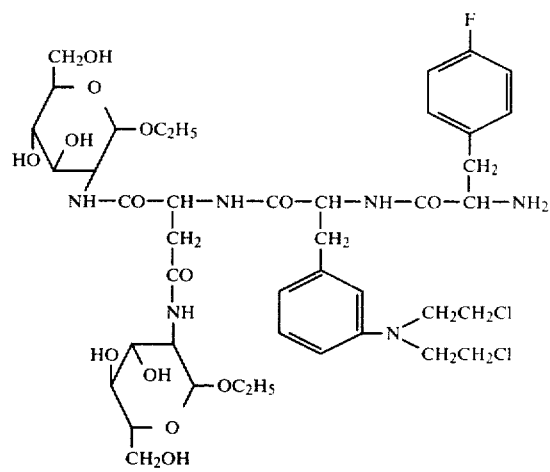

and its salts with organic or inorganic acids physiologically tolerated. The antineoplastic activity of the compounds of the present invention is not affected in the gastrointestinal tract and hence they can be effectively administered orally.

8 Claims, No Drawings

N-ACYL DERIVATIVES OF GLUCOSAMINE HAVING ANTITUMOR CHEMOTHERAPEUTIC ACITIVITY

RELATED APPLICATIONS

This application is a continuation-in-part application of copending U.S. Ser. No. 929,237, filed July 31, 1978 now U.S. Pat. No. 4,216,208, patented Aug. 5, 1980.

BACKGROUND OF THE INVENTION

The present invention relates to N-acyl derivatives of an amino sugar with an oligopeptide, endowed with antitumor chemotherapeutic activity, and to pharmaceutical compositions containing said derivatives.

Antitumor chemotherapy has been and still is an object of intensive research. Certain positive results have undoubtedly been achieved, especially by means of polychemotherapy realized by associating different active substances according to carefully developed protocols. However, the ideal therapy has not yet been found. The need to find new active substances has been particularly emphasized. All the foregoing justifies continuous research directed towards preparing new chemotherapeutic compounds active against tumors. There are already known peptides having antitumor activity, consisting of both normal and antimetabolic amino acids, coupled by means of a peptide bond. Such peptides have for years been in therapeutic use with favorable results both in monochemotherapy and in polychemotherapy. However, there adoption encounters obstacles of various kinds, which are connected, among other things, with the impossibility of being administered by the oral route because of inactivation of the said peptides in the gastrointestinal tract.

In my copending U.S. application Ser. No. 929,237 there is disclosed a series of compounds possessing antitumor activity against transplanted tumors in animals characterized by the presence of a molecule of a glucosamine. The antitumor chemotherapeutic activity of those compounds is also reported in an article by the inventor entitled "N-Acyl Derivatives of Glucosamine with Oligo-Peptides," *Current Chemotherapy*, American Society of Microbiology, p. 1183 (April 1978). The glucosamine is used as a carrier of an antitumor-active compound wherein the antitumor-active molecule is bound to the —$NH_2$ of the glucosamine. For example, the amino group of the glucosamine is acylated by the carboxyl group of an antitumor amino acid or peptide. The compounds disclosed in said copending application and in said article are of the general formula:

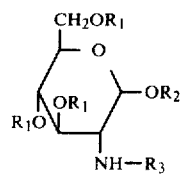

where
$R_1$ is a hydrogen atom or an acetyl group,
$R_2$ is a hydrogen atom, an acetyl group, aliphatic ($C_1$–$C_6$) group or a benzyl group, and
$R_3$ is m-di(2-chloroethyl)amino-L-phenylalanine, or L-methionyl-m-di(2-chloroethyl)amino-L-phenylalanyl-p-fluoro-L-phenylalanine, or p-fluoro-L-phenylalanyl-m-di(2-chloroethyl)amino-L-phenylalanyl-L-proline, or m-di(2-chloroethyl)amino-L-phenylalanyl-L-methionyl-p-fluoro-L-phenylalanine.

By investigating the chemotherapeutic effect afforded by substituting other peptides besides those listed above at the $R_3$ position in the above-mentioned formula, novel compounds were obtained wherein an oligopetide is covalently bonded to two molecules of a D-hexosamine or other amino sugars such as glucosamine, galactosamine, or mannosamine through peptide linkages between the amino groups of the amino sugar molecules and the two carboxylic acid groups of the aspartic acid portion of the oligopeptide.

The resulting N-acyl derivatives of the amino sugars of the present invention are not inactivated in the gastrointestinal tract and are useful in controlling transplanted neoplasms in animals.

SUMMARY OF THE INVENTION

It is an object of the present invention to provide novel compounds which are effective in controlling transplanted neoplasms in animals.

It is another object of the present invention to provide novel compounds which can be administered orally without undergoing antitumor deactivation in the gastrointestinal tract.

It is still another ojbect of the present invention to provide pharmaceutical compositions which are effective in controlling neoplasms and which contain at least one of the novel compounds of the present invention as an active ingredient.

These and other objects of the present invention are accomplished by condensing an amino sugar with an oligopeptide to form via peptide linkages, compounds wherein the oligopeptide sequence L-aspartoyl-m-di(2-chloroethyl)amino-L-phenylalanyl-p-fluoro-L-phenylalanine is bonded to two amino sugar molecules through the two carboxyl groups of the aspartic acid portion of the oligopeptide group.

DESCRIPTION OF THE PREFERRED EMBODIMENTS

Compounds which achieve the objects of the present invention are:

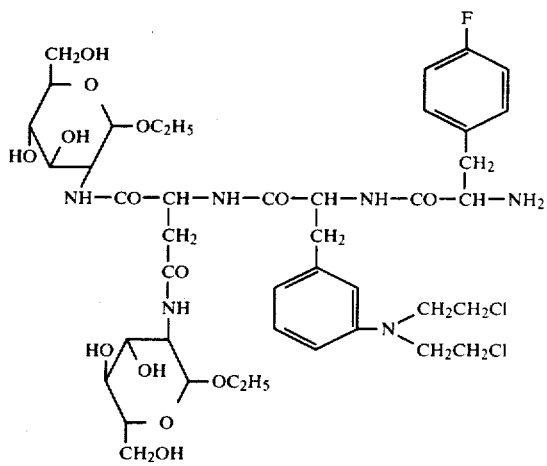

and salts thereof with an organic or inorganic acid physiologically tolerated.

The preferred inorganic acid for forming the salts of the present invention is hydrochloric acid. Acetic acid is the preferred organic acid for forming the salts of the present invention.

The novel compounds are constituted by two molecules of glucosamine (actually, a mixture of the two α and β anomers the latter in general being prevalent) which are each bonded by peptide linkage (—NH—CO—) to an oligopeptide molecule of the formula:

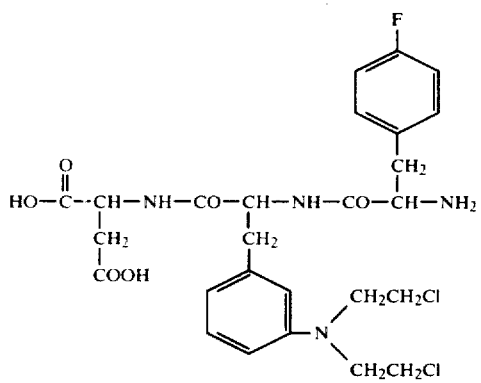

The peptide bond is between the amino group of the glucosamines and the terminal carboxylic acid groups of the aspartic acid portion of the oligopeptide. The glucosamines are carriers of the antitumor-active oligopeptide. It is in particular noted that, to have good antitumor activity, all of the amino acids used for the peptide synthesis and so forming the peptide moiety, must belong to the L-configuration.

The compounds of the present invention are prepared by the same general method described in my U.S. Pat. No. 4,216,208 at col. 6 line 41 to col. 7 line 34 which portion is herein incorporated by reference. Thus, the compounds of the present invention are prepared by protecting the terminal amino group of the oligopeptide by acylation to form a Schiff base, as by reaction with carbobenzoxy chloride or formyl chloride. The thus acylated oligopeptide, aspartyl-m-di(2-chloroethyl)amino-L-phenylalanine-N-formyl-p-fluoro-phenylalanine(Asp-mMphe-M-For-p-F-Phe) is reacted with two moles of D-glucosamine per mole of the oligopeptide in the presence of dicyclohexylcarbodiimide (DCC) plus hydroxysuccinimide (HDS) whereby condensation to form the peptide linkage (—NHCO—) occurs. The terminal amino group is then deprotected by reagents which do not disturb peptide linkages. For example, deprotection may be achieved by catalytic hydrogenation with Pd/C and hydrogen gas or by hydrolysis with alcoholic hydrochloric acid.

The oligopeptide moiety of the compounds of the present invention is synthesized according to methods already known. Synthesis of a dipeptide is by means of condensation via DCC between two amino acids blocked respectively at the amino group and the carboxyl group, followed by deprotection of the carboxyl group and condensation with the amino group of a third amino acid blocked at the carboxyl group by means of DCC. In this way an acylated peptide is obtained. For the purpose of selectively protecting the amino functional groups, the amino group is acylated, for example with formic acid or with carbobenzoxy chloride. The carboxyl groups are protected by means of esterification to the methyl, ethyl, hexyl or benzyl ester, which are then cleaved by cautious saponification.

A detailed description of the synthesis of a compound of the present invention is given in the following example. Symbols conventionally used in biochemistry to designate amino acids or amino acid moieties are used herein. For example, Asp=L-aspartic acid, Phe=L-phenylalanine, GlcN=D-glucosamine, etc. Additional abbreviations used herein are: mMphe=meta-L-phenylalanine mustard (i.e., m-di(2-chloroethyl)amino-L-phenylalanine, DCC=dicyclohexylcarbodiimide, DCU=dicyclohexylurea, HDS=hydroxysuccinimide). Unless otherwise indicated, all percentages, proportions and ratios are by weight and all temperatures are in ° C. Also, the single compounds were analyzed and controlled by means of elemental analysis (chlorine-bonded, either with covalent or ionic bond-nitrogen, possibly sulphur), specific optical rotation, thin layer chromatography (TLC) (silica gel G), UV spectrophotometry, IR spectrometry.

EXAMPLE

Ethyl-D-glucosamyl-L-aspartoyl(β-ethoxy)-D-glucosamyl-m-di-(2-chloroethyl)amino-L-phenylalanyl-p-fluoro-phenylalanine The synthesis of this compound is accomplished through the following steps:

1. Diethyl aspartyl-m-di(2-chloroethyl)amino-L-phenylalanine (Intermediate I)

To a cooled solution of 8.44 gms (44.6 mmoles) of diethyl aspartic acid in 160 ml of chloroform (or tetrahydrofuran) are added 19.63 gms (44.6 mmoles) of N-carbobenzoxy-m-di(2-chloroethyl)amino-L-phenylalanine and 10 gms (48.6 mmoles) of DCC with stirring and cooling. After a night at room temperature the DCU is removed, the solution is washed with dilute acetic acid, then with water and a saturated solution of $NaHCO_3$. Then the solvent is evaporated and the residue is purified on a Kieselgel column following elution with a mixture of chloroform-ethylacetate. The final dipeptide product is crystallized from boiling ethanol $[\alpha]_D^{21} = +37.3$ (C=1 chloroform) m.p. 99°-101° C.

To remove the carbobenzoxy group of the dipeptide product, a suspension is prepared by admixing 200 ml of methanol with 5% glacial acetic acid plus 1 gm of Palladium and 6.2 mmoles (3.8 gm) of the dipeptide. Under electromagnetic stirring a stream of hydrogen is passed through the suspension until the evolution of $CO_2$ ends. Then the catalyst is removed and the solution is evaporated under vacuum. The residue, dissolved in ethanolic HCL (5%) and treated with anhydrous ethyl ether gives the solid product.

Analytical data: $C_{21}H_{31}Cl_2N_3O_5 \cdot HCl$ (512.8); calc. N 8.19 Cl 20.74; found N 8.21 Cl 20.81.

2. Diethyl aspartyl-m-di(2-chloroethyl)amino-L-phenylalanyl-N-formyl-P-fluoro phenylalanine (Intermediate II)

To a mixture of 15.2 gms (32 mmoles) of diethyl-Asp-m-L-MPhe (Intermediate I), and 6.3 gms (29.9 mmoles) of N-Formyl p-Fluoro-L-Phe dissolved in 150 ml of tetrahydrofuran, 6.7 gms (32.88 mmoles) of DCC are added with external cooling and electromagnetic stirring. Then the external cooling is stopped and the stirring is continued for 4-5 hours. DCU is removed by filtration. The tetrahydrofuran solution is concentrated. DCU separated during the concentration is removed by filtration. The final solid product is crystallized twice from ethanol and dried under infra-red radiation.

Analytical data: $C_{31}H_{39}FCl_2N_4O_7$ (669.6); calc. N 8.37 Cl 10.59, found N 8.42 Cl 10.62.

3. Aspartyl-m-di(2-chloroethyl)amino-L-phenylalanyl-N-formyl-p-fluoro phenylalanine (Intermediate III)

10 gms of the tripeptide of the second step (Intermediate II) are dissolved in 60 ml of DMF and filtered to give a clear solution. To this solution with external cooling 30 ml of 1 N NaOH are added slowly (half an hour). After 1 hour of stirring, the solution is neutralized by the addition of 1 N HCl, added slowly and with external cooling. Towards the end of the operation, the acid tripeptide precipitates and is collected and washed with ether.

Analytical data: $C_{27}H_{31}FCl_2N_4O_7$ (545.6); calc. N 10.27 Cl 12.99, found N 10.25 Cl 13.07.

4. D-glucosamyl-aspartoyl (β-ethoxy)-D-glucosamyl)-m-di-(2-chloroethyl) amino-L-phenylalanyl-N-p-fluoro-phenylalanine (Intermediate IV)

62 gms of Glucosamine hydrochloride (288 mmoles) are added to 130 ml of water at room temperature and stirred for one hour. Then 24.4 gms of $NaHCO_3$ (144 mmoles) are added in small portions under stirring for about 1 hour. After this time the D-glucosamine is dissolved. A solution is made by admixing 82 gms of the tripeptide obtained in the third step (Intermediate III) with 850 ml of DMF to which 30 gms of DCC and 25 gms of HDS are added. When all the compounds are well dissolved the solution of D-Glucosamine is added and kept under continuous stirring for at least 7 hours. During the process, chromatography (TLC) is used. At the end, DCU formed is eliminated by filtration, then the solution is dropped in 2 liters of cold water under stirring. The precipitate is collected by filtration and dissolved in 300 ml of DMF and again precipitated as before. The precipitate is washed with absolute ethanol and then with ether and dried.

Analytical data: $C_{39}H_{53}FCl_2N_6O_{15}$ (867.7); calc. N 9.69 Cl 8.17. found N 9.68 Cl 8.21.

5. Ethyl-D-glucosamyl-L-aspartoyl(β-ethoxy)-D-glucosamyl)m-di(2-chloroethyl-amino)-L-phenylalanyl-p-fluoro-L-phenylalanine 10 gms of the pentapeptide from the fourth step (Intermediate IV) are dissolved in 1.2 N HCl in absolute ethanol. The mixture is stirred for 24 hours at room temperature. Then the reaction mixture is treated with charcoal, filtered and admixed with 400 ml of ether. The precipitate is washed with ether, then dissolved in warm ethanol. Upon cooling, a precipitate is obtained. After drying, 8 gms of product are obtained.

Analytical data: $C_{38}H_{53}FCl_2N_6O_{14}HCl$ (934.3); Calc. N 8.99 Cl 11.38, found N 9.04 Cl 11.38.

The experimental models employed for the evaluation of th chemotherapeutic activity of the compounds of the present invention are the same as those used in my copending patent application Ser. No. 929,237 at pages 11 to 13.

The chemotherapeutic activity of the compound ethyl-D-glucosamyl-L-aspartoyl(β-ethoxy)-D-glucosamyl)m-di(2-chloroethylamino)-L-phenylalanyl-p-fluoro-L-phenylalanine was evaluated by conducting trials on mice injected with cells of Leukemia 1210 according to the procedure established in *Cancer Chemotherapy Reports* 1972, Vol. 3, No. 2: Protocols for Screening Chemical Agents and Natural Products Against Animal Tumors and other Biological Systems (Third Edition, National Cancer Institute, Bethesda, Maryland. The experimental model employed for the evaluation is:

Determination of the MST (Mean Survival Time) of BDGI mice inoculated intraperitoneally with $10^5$ cells of lymphoid Leukenia L 1210 deriving from regular implants in DBA2 mice. The MST was determined both on the controls and on the animals treated, and thereafter an evaluation was made of the ILS (Increased Life Span) according to *Cancer Chemotherapy Reports* 1972, Vol. 3, No. 2 (Protocols for Screening Chemical Agents and Natural Products Against Animal Tumors and other Biological Systems—Third Edition, National Cancer Institute, Bethesda, Maryland). In this case, the compounds were tested only after oral administration starting from the 3rd day after implant of the tumor and continuing on the 17th, 25th and 35th day. On the 52nd day, any surviving animals were sacrificed and the experiment discontinued and evaluated.

A typical experiment on ten mice gave the following results:

Mean Survival Time (MST) = 32.7 days
Increase in Life Span (ILS) = 186.4 days
T/C% (Ratio, expressed as percent, of the MST of the treated group divided by the MST of the control group) = 311.4%

The formula for the calculation of mean survival time is:

$$\frac{S + 6S_5}{S_5} = \frac{267 + (6 \times 10)}{10} = \frac{327}{10} = 32.7$$

wherein

Day A = Day on which deaths are no longer considered due to drug toxicity - For Leukemia L 1210 day A = day 6

Day B = This day cannot be considered here because all control animals died within the 11th day and survivors were not observed.

S = The total of survivors from 6th day onwards
S(A-1) = Number of survivors at the end of day 5
(A-1) = $S_5$ The ILS and the ratio T/C% are calcuated as follows:

I.L.S. = 311.4 − 125 = 186.4 days
T/C% = (32.7/10.5) × 100 = 311.4%

The protocol of this experiment is presented in the Table:

TABLE

EFFECT OF ETHYL-D-GLUCOSAMYL-L-ASPARTOYL (β-ETHOXY)-D-GLUCOSAMYL)M-DI(2-CHLOROETHYL-AMINO)-L-PHENYLALANYL-P-FLUORO-L-PHENYLALANINE, ADMINISTERED ORALLY, ON SURVIVAL IN TUMOR-BEARING MICE (LEUKEMIA L 1210)

| Day From Inoculum | Treatment | Dosage mg/Kg | Survivors | M.S.T. | T/C % | I.L.S. | mMPhe Content In mg/Kg |
|---|---|---|---|---|---|---|---|
| 0 | Inoculum: $10^5$ cells i.p. | | 10 | | | | |
| 1 | | | 10 | | | | |
| 2 | | | 10 | | | | |
| 3 | Eth—GlcN—Asp—β-ethoxy-GlcN—mMphe—p-F—Phe | 25 | 10 | | | | 8.5 |
| 4 | | | 10 | | | | |
| 5 | | | 10 | | | | |
| 6 | | | 10 | | | | |
| 7 | | | 10 | | | | |
| 8 | | | 10 | | | | |
| 9 | | | 10 | | | | |
| 10 | | | 10 | | | | |
| 11 | | | 10 | | | | |
| 12 | | | 10 | | | | |
| 13 | | | 10 | | | | |
| 14 | | | 10 | | | | |
| 15 | | | 10 | | | | |
| 16 | | | 10 | | | | |
| 17 | Eth—GlcN—Asp—β-ethoxy-GlcN—mMphe—p-F—Phe | 15 | 10 | | | | 5.1 |
| 18 | | | 10 | | | | |
| 19 | | | 8 | | | | |
| 20 | | | 8 | | | | |
| 21 | | | 6 | | | | |
| 22 | | | 6 | | | | |
| 23 | | | 6 | | | | |
| 24 | | | 6 | | | | |
| 25 | Eth—GlcN—Asp—β-ethoxy-GlcN—mMphe—p-F—Phe | 10 | 6 | | | | 3.4 |
| 26 | | | 6 | | | | |
| 27 | | | 6 | | | | |
| 28 | | | 6 | | | | |
| 29 | | | 6 | | | | |
| 30 | | | 5 | | | | |
| 31 | | | 5 | | | | |
| 32 | | | 5 | | | | |
| 33 | | | 5 | | | | |
| 34 | | | 4 | | | | |
| 35 | Eth—GlcN—Asp—β-ethoxy-GlcN—mMphe—p-F—Phe | 5 | 4 | | | | 1.7 |
| 36 | | | 4 | | | | |
| 37 | | | 4 | | | | |
| 38 | | | 4 | | | | |
| 39 | | | 4 | | | | |
| 40 | | | 3 | | | | |
| 41 | | | 3 | | | | |
| 42 | | | 2 | | | | |
| 43 | | | 2 | | | | |
| 44 | | | 2 | | | | |
| 45 | | | 2 | | | | |
| 46 | | | 2 | | | | |
| 47 | | | 2 | | | | |
| 48 | | | 2 | | | | |
| 49 | | | 1 | | | | |
| 50 | | | 1 | | | | |
| 51 | | | 1 | | | | |
| 52 | | | 0 | | | | |
| | RESULTS | | | 32.7 | 311.4 | 186.4 | |

The results demonstrate that the present invention achieves a substantial advance in experimental chemotherapy. It has been unexpectedly found that an oligopeptide containing two moles of amino sugar in its molecule is active against tumors by the oral route.

The compounds of the present invention can be administered orally or parenterally, in a single dose or in successive doses, in pharmaceutically acceptable amounts. In the above experiment a descending range of doses was used: from 25 mg/kg to 15, 10, and 5 mg/kg totaling 55 mg/kg. As is known in the art, the pharmacologically active dose varies according to the animal species, the tumor which is implanted, and so on. The pharmaceutical compositions of the present invention comprise at least one of the compounds of the present invention as an active ingredient in a known pharmaceutical carrier.

I claim:

1. An N-acyl derivative of D-glucosamine selected from the group consisting of a compound of the formula:

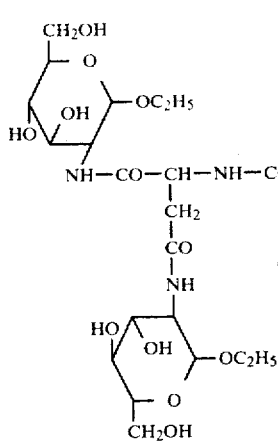
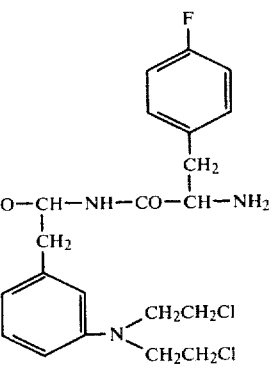

or a salt thereof with an organic or inorganic acid physiologically tolerated.

2. An N-acyl derivative as claimed in claim 1 which is a hydrochloric acid salt.

3. An N-acyl derivative as claimed in claim 1 which is an acetic acid salt.

4. A pharmaceutical composition which is effective in controlling transplanted neoplasms in animals comprising an N-acyl derivative as claimed in any one of claims 1, 2, or 3 as an active ingredient in a pharmaceutically effective amount in a pharmaceutical carrier.

5. A pharmaceutical composition which is effective in controlling transplanted neoplasms in animals comprising a mixture of N-acyl derivatives as claimed in claim 1 as an active ingredient in a pharmaceutically effective amount in a pharmaceutical carrier.

6. An N-acyl derivative of an amino sugar with the oligopeptide group L-aspartoyl-m-di(2-chloroethyl)amino-L-phenylalanyl-p-fluoro-L-phenylalanine wherein each of the two carboxyl groups of the aspartic acid portion of said oligopeptide group is bonded by peptide linkage to a molecule of the amino sugar.

7. An N-acyl derivative as claimed in claim 6 wherein said amino sugar is a D-hexosamine.

8. An N-acyl derivative as claimed in claim 6 wherein said amino sugar is galactosamine or mannosamine.

* * * * *